United States Patent
Schalapski et al.

(10) Patent No.: US 10,501,396 B2
(45) Date of Patent: Dec. 10, 2019

(54) CONTINUOUS PRODUCTION METHOD FOR 2-METHYLENE ALKANALS

(71) Applicant: OXEA GmbH, Monheim (DE)

(72) Inventors: Kurt Schalapski, Oberhausen (DE); Jan-Henry Rahe, Herten Westerholt (DE); Christoph Balzarek, Krefeld (DE); Gregor Meier, Duisburg (DE); Heinz Strutz, Moers (DE)

(73) Assignee: OXEA GMBH, Monheim (DE)

( * ) Notice: Subject to any disclaimer, the term of this patent is extended or adjusted under 35 U.S.C. 154(b) by 0 days.

(21) Appl. No.: 16/325,950

(22) PCT Filed: Sep. 5, 2017

(86) PCT No.: PCT/EP2017/072234
§ 371 (c)(1),
(2) Date: Feb. 15, 2019

(87) PCT Pub. No.: WO2018/059887
PCT Pub. Date: Apr. 5, 2018

(65) Prior Publication Data
US 2019/0218166 A1    Jul. 18, 2019

(30) Foreign Application Priority Data
Sep. 30, 2016    (EP) .................................... 16191892

(51) Int. Cl.
| | | |
|---|---|---|
| *C07C 45/75* | (2006.01) | |
| *B01J 19/00* | (2006.01) | |
| *B01J 19/24* | (2006.01) | |
| *C07C 47/21* | (2006.01) | |

(52) U.S. Cl.
CPC ........... *C07C 45/75* (2013.01); *B01J 19/0013* (2013.01); *B01J 19/2415* (2013.01); *C07C 47/21* (2013.01); *B01J 2219/00051* (2013.01); *B01J 2219/00164* (2013.01); *B01J 2219/3322* (2013.01)

(58) Field of Classification Search
CPC ...... C07C 45/75; B01J 19/003; B01J 19/2415
See application file for complete search history.

(56) References Cited

U.S. PATENT DOCUMENTS

| | | |
|---|---|---|
| 4,263,460 A | 4/1981 | Weber et al. |
| 4,950,800 A | 8/1990 | Weber et al. |
| 6,340,778 B1 | 1/2002 | Bueschken et al. |
| 2014/0343280 A1 | 11/2014 | Richter et al. |
| 2016/0280624 A1 | 9/2016 | Burghardt et al. |
| 2017/0275227 A1 | 9/2017 | Burghardt et al. |

FOREIGN PATENT DOCUMENTS

| | | |
|---|---|---|
| CN | 105693491 A | 6/2016 |
| DE | 3744212 A1 | 7/1989 |
| DE | 19957522 A1 | 5/2001 |
| EP | 2883859 A1 | 6/2015 |
| EP | 2998284 A1 | 3/2016 |
| WO | 2013079614 A2 | 6/2013 |
| WO | 2014170223 A1 | 10/2014 |

OTHER PUBLICATIONS

International Preliminary Report on Patentability dated Apr. 11, 2019.
Written Opinion of the International Searching Authority (translation) dated Oct. 16, 2017.
International Search Report dated Oct. 16, 2017.
Written Opinion dated Oct. 16, 2017.

*Primary Examiner* — Sikarl A Witherspoon
(74) *Attorney, Agent, or Firm* — Michael Ferrell

(57) ABSTRACT

The present invention relates to the continuous production of 2-methylene alkanals in a tube reactor, wherein in the 2-position non-branched alkanals are reacted with formaldehyde under acid-base catalysis in the presence of secondary amines and carboxylic acids under laminar flow conditions.

20 Claims, 1 Drawing Sheet

CONTINUOUS PRODUCTION METHOD FOR 2-METHYLENE ALKANALS

CLAIM FOR PRIORITY

This patent application is a National Stage entry of international application PCT/EP2017/072234, filed Sep. 5, 2017. Application PCTEP2017072234 claims priority of European application EP16191892.5, filed Sep. 30, 2016. The priorities of applications PCT/EP2017/072234 and EP16191892.5 are claimed and the disclosures thereof are incorporated by reference.

TECHNICAL FIELD

The present invention relates to the continuous production of 2-methylene alkanals in a tube reactor, wherein in the 2-position non-branched alkanals are reacted with formaldehyde under acid-base catalysis in the presence of secondary amines and carboxylic acids under laminar flow conditions.

BACKGROUND

Due to their high functionality, 2-methylene alkanals are valuable intermediates in the industrial organic chemistry. By selective hydrogenation of the double bond, 2-methyl-alkanals can be obtained which play an important role in the fragrance industry. A further important reaction of this class of substances is obtained, for example, by oxidation of the aldehyde function into then unsaturated carboxylic acids, which are used on a large scale for the production of plastics, lubricating oils or textile auxiliary agents.

It is known to produce 2-methylene alkanals by reacting unbranched n-aldehydes with formaldehyde. The reaction is carried out in the presence of secondary amines in the form of a Mannich condensation reaction, wherein at first a Mannich base is formed under dehydration

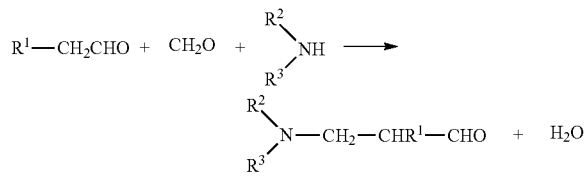

from which 2-methylene alkanals are ultimately obtained by separation of the secondary amine:

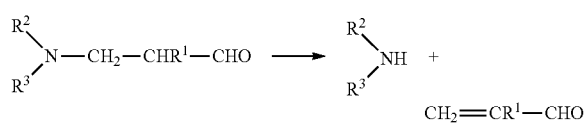

(Methoden der Organischen Chemie, Houben Weyl, Georg Thieme Verlag, 4th edition, 1954, volume VII, part 1, pages 93-94).

The condensation reaction can in this case, as such, be carried out only with the classes of substances listed in the abovementioned reaction schemes or else can be catalyzed by the addition of acids or further bases.

DE 2855 506 A1 discloses a possibility for reacting alkanals only in the presence of catalytic amounts of secondary amines.

WO199320034 A1 describes the aldolization of C3 to C10 aldehydes in a continuously operated agitated vessel with subsequent distillation. Substituted acroleins are produced, wherein hydroxides or carbonates are used as additional catalysts.

An acid-base-catalyzed production method is disclosed, for example, in DE3744212 A1. In the process described therein, a C5 alkanal mixture obtained during the hydroformylation of isomeric butenes, is reacted during a reactive distillation with an aqueous formaldehyde solution in the presence of a secondary amine and a mono-, di- or polycarboxylic acid.

Just as diverse as the selection of the possible reaction conditions are also the operation modes and types of reactors which can be used for the production. For example, both batch and continuous processes are found in the patent literature, wherein the reaction is carried out, inter alia, in agitated vessels, agitated vessel cascades and also tube reactors. An example of an optionally continuous or batch reaction in an agitated vessel is given in the abovementioned DE 2855 506 A1. A continuous reaction in a tube reactor is described, for example, in DE 199 57 522 A1.

For the reaction of the employed aldehydes with formaldehyde in the presence of a catalyst, agitated vessels are typically used to ensure an intensive mixing of the organic and the aqueous phase. However, the reaction in agitated vessels is disadvantageous, since the discontinuous reaction control, in addition to heating and cooling processes, also exhibits a non-uniform amount of reaction heat, which can lead to suboptimal reaction results. In addition, the operation of mechanically moving parts is typically maintenance intensive and susceptible to repairs. On the other hand, a continuous reaction control within an agitated vessel or an agitated vessel cascade appears to be problematic due to the liquid multi-phase system because an undesirable one-sided discharge of one phase can lead to an enrichment of the other phase and thus leads to disadvantages by fluctuations of the average dwell time with respect to the conversion rate, selectivity and space-time yield.

SUMMARY OF INVENTION

It is the object of the present invention to provide a continuous production process for 2-methylene alkanals, which requires only low technical effort, is not very energy intensive and is characterized by high space-time yields.

This object is achieved by a method according to claim 1. Preferred embodiments of the method are provided in the dependent claims.

According to the invention, the object is achieved by a method for the producing 2-methylene alkanals of the general formula I

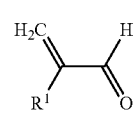

Formula I wherein $R^1$ is an aliphatic residue, by reacting alkanals of the general formula II

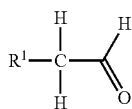

Formula II with an aqueous formaldehyde solution in the presence of at least one secondary amine and at least one carboxylic acid, wherein the educts are reacted in a liquid/liquid two-phase system, and wherein the reaction is carried out continuously within a tube reactor under laminar flow conditions with a Reynolds number of greater than or equal to 10 and less than or equal to 2320. Surprisingly, it has been found that within a continuous process in a tube reactor in a strictly laminar operation mode under acid-base catalysis, very high space-time yields at desired 2-methylene alkanals can be realized. As a result, the production plants can be dimensioned smaller, and advantageously high product quantities can be obtained under low investment and operating costs. This result is surprising, since in the prior art technical solutions are emphasized as particularly preferred in which large phase boundary interfaces between aqueous and organic phases are established. According to the general rules of reaction kinetics, large phase boundary interfaces should contribute to a high mass exchange between organic and aqueous phases and consequently lead to high yields. In order to obtain these large phase boundary interfaces, turbulent operation modes are proposed which are intended to ensure a consistently good mixing of the organic and the aqueous phase. In the case of agitated vessels and/or cascades, as already mentioned above, this good mixing is associated with a high technical effort and high operating costs. An equivalent view should also apply to tube reactors, wherein here, too, a turbulent flow regime should contribute to a higher phase boundary interface and thus to higher conversion rates. Moreover, typically a turbulent regime allows a much better heat dissipation, which is quite helpful in the selectivity control of the exothermic reaction under consideration. Without being bound by theory, the high space-time yield under "only" laminar flow conditions, that is to say in the case of a potentially lower phase boundary interface/exchange surface compared to turbulent operation modes, is achieved in particular by the acid-base catalysis employed according to the invention. Apparently, the carboxylic acids which can be used according to the invention are capable of stabilizing interfaces in the organic/aqueous two-phase system and contributing to a high mass exchange. This could partly also be caused by the amphiphilic character of the carboxylic acids which could contribute to a stabilization in a laminar flow regime of formed phase boundary interfaces. In addition, the selected multi-phase flow regime allows a sufficient stability of the reaction temperature, which is not self-evident with respect to the strictly laminar operation mode.

The useable alkanals according to formula II can generally be aldehydes with a carbon number of C3-C15 ($R^1$ is an aliphatic organyl residue with 1 to 13 C atoms). The starting compounds can therefore be regarded as short or medium aldehydes. In particular, aldehydes can be used which are obtained from known hydroformylation reaction or oxo reaction of the corresponding olefins reduced by one carbon atom. In this hydroformylation reaction, the feed olefin is reacted with a mixture of carbon monoxide and hydrogen in the presence of transition metal catalysts such as cobalt or rhodium catalysts. The reaction can be carried out either without or with organophosphorus compounds, such as triphenylphosphine, as complex ligands and is described in detail in the technical literature (Ullmans's Encyclopedia of Industrial Chemistry, 5th edition, 1985, VCH Verlagsgesellschaft mbH, Vol. A1, pages 326-331; 5th ed., 1991, VCH Verlagsgesellschaft mbH, Vol. A18, pages 321-327). In the hydroformylation reaction of terminal olefins, an isomeric mixture of alkanals is obtained, wherein in addition to the alkanals of the general formula II also 2-methyl alkanals and further alkanals are formed. The relative proportions of these isomers depend on the hydroformylation conditions.

The alkanals with 3 to 15 carbon atoms ($R^1$ is an aliphatic organyl residue with 1 to 13 C atoms) to be used in the method according to the invention are usually the products from the hydroformylation of olefins, for example the hydroformylation products from the reaction of hexene-1, heptene-1, octene-1, nonene-1, decene-1, undecene-1 or dodecene-1. According to the method according to the invention, relatively short-chain aldehydes with 3 to 5 carbon atoms in the molecule, for example propionaldehyde, n-butyraldehyde, n-pentanal or 3-methylbutanal, can be reacted. Moreover, aldehydes with higher C numbers, for example n-heptanal, n-octanal, n-nonanal, 3,5,5-trimethylhexanal-1, n-decanal, n-undecanal, n-dodecanal or n-tridecanal, can be reacted. The alkanals to be used, however, must include at least one alkanal with two hydrogen atoms at the C carbon atom adjacent to the carbonyl function (2-position, α-position) in order to enable the formation of the 2-methylene alkanals.

Furthermore, it has surprisingly been found that also alkanal mixtures which comprise a plurality of educt alkanals of the formula II or mixtures of different alkanals can be reacted by the above method. For example, the described method is applicable to a mixture of n-undecanal and 2-methyl-decanal, in which only the n-aldehyde reacts and the methyl-branched aldehyde behaves substantially inert. In particular, the method can also be used to selectively increase the boiling point of alkanals with two hydrogen atoms in the alpha position relative to the carbonyl group by conversion into the corresponding 2-methylene alkanals, wherein these can be separated more easily from mixtures due to their then higher boiling point. This may be important, for example, in the separation of a 2-methylbutanal and 3-methylbutanal mixture. Particularly good results with high space-time yields are obtained, however, in the presence of only one educt according to formula II in the reaction solution.

In the formulas I and II, $R^1$ denotes an aliphatic residue. These mean linear, branched or cyclic saturated hydrocarbon residues with a carbon number of C1-C13. Substitutions in the chain, for example, with one or more halogen function(s) or one or more hydroxyl group(s) are possible.

The reaction of alkanals of the general formula II involves reacting the educt alkanal under acid-base catalysis in the presence of a secondary amine and a carboxylic acid into the corresponding 2-methylene alkanal.

As an aqueous formaldehyde solution formalin solutions can be used, for example, in a concentration of 20-49% by weight, preferably 25 to 35% by weight. Herein, based on one mol educt alkanal of formula II formaldehyde can be used, for example, in a stoichiometric amount. However, the reaction can also be carried out in an excess of formaldehyde, preferably up to 20 mol-% and in particular up to 10 mol-%.

Herein, the reaction is carried out in the presence of at least one secondary amine. As suitable secondary amines those of the formula

come into consideration, wherein $R^2$ and $R^3$ may be identical or different and are an alkyl residue with 1 to 12, advantageously 1 to 10, preferably 1 to 6 carbon atoms which may be optionally substituted with one or more heteroatoms, preferably with hydroxyl and/or secondary or tertiary amine. $R^2$ and $R^3$ can form with the adjacent carbon atom members of an advantageously 5- or 6-membered ring which may also contain a nitrogen or oxygen atom. As secondary amines, for example: N-methyl-, N-ethyl-, N-propyl-, N-isopropyl-, N-butyl-, N-sec-butyl, N-tert-butyl, N-pentyl, N-hexyl, N-heptyl, N-octyl, N-nonyl, N-decyl-(2-hydroxyethylamine); corresponding amines which are substituted twice equally or differently by an aforementioned substituent; piperidine, morpholine, pyrrolidine, piperazine, N-methylpiperazine; N, N'-dimethylethylenediamine come into consideration.

Preferably (2-hydroxyethyl)-N-methylamine, N-ethyl(2-hydroxyethyl)amine, (2-hydroxyethyl)-N-isopropylamine, N-butyl(2-hydroxyethyl)amine, (2-hydroxypropyl)-N-isopropylamine, (3-hydroxypropyl)-N-isopropylamine, N-butyl-(2-hydroxypropyl)amine, N-butyl-(3-hydroxypropyl)amine, (2-hydroxypropyl)-N-isobutylamine, (3-hydroxypropyl)-N-isobutylamine, N,N-bis(2-hydroxyethyl)amine, bis(2-hydroxypropyl)amine, bis(3-hydroxypropyl)amine, N,N'-bis(2-hydroxyethyl)ethylenediamine, piperazine, N-methylpiperazine, as well as the dialkylamines di-n-propylamine, di-n-pentylamine, di-n-hexylamine and particularly preferred di-n-butylamine can be used.

Herein, the reaction is carried out acid-base catalyzed in the presence of at least one carboxylic acid. As carboxylic acids usually aliphatic mono-, di- and polycarboxylic acids with 2 to 10 carbon atoms are used. Dicarboxylic acids and polycarboxylic acids, including preferably tricarboxylic acids, can also be aromatic and aliphatic carboxylic acids. The reaction is preferably carried out in the presence of monocarboxylic acids. Suitable monocarboxylic acids are, for example, acetic acid, propionic acid, n-butyric acid, isobutyric acid, 2-ethylbutyric acid, 2-methylpentanoic acid, 2-ethylhexanoic acid and isononanoic acid. The polycarboxylic acids that can be used in the method according to the invention include pimelic acid, suberic acid, azelaic acid, sebacic acid, nonanedicarboxylic acid, decanedicarboxylic acid, butane tetracarboxylic acid, pentane-1,3,5-tricarboxylic acid, 3-hydroxyglutaric acid, saccharic acid, α,α'-dihydroxy-adipic acid, preferably oxalic acid, succinic acid, glutaric acid, adipic acid, malic acid, tartaric acid, butane-1,2,4-tricarboxylic acid, 3-ethylpentane-1,3,5-tricarboxylic acid, citric acid, trimellitic acid, butanetetracarboxylic acid, pyromellitic acid, terephthalic acid, isophthalic acid and fumaric acid.

In a particularly preferred embodiment, the reaction of the alkanal with formaldehyde can be carried out in the presence of di-n-butylamine and n-butyric acid as catalyst.

The reaction of the educts is carried out in a liquid/liquid two-phase system. Due to the combination of an aqueous phase and an organic phase a two-phase system is formed in which the organic phase is dispersed in the aqueous phase. Without being bound by theory, it is assumed that due to the distribution coefficients the carboxylic acids and the secondary amine which can be used according to the invention are mainly present in a form dissolved in the organic phase.

In the course of the reaction, formaldehyde then transits into the organic phase and reacts with the alkanal. According to the solubility of formaldehyde in the water the aqueous phase has a residual content of formaldehyde.

According to the invention, the reaction is carried out continuously within a tube reactor. This means that the supply of the educts and the discharge of the products are carried out continuously, for example as a continuous stream of the different solutions into and out of the tube reactor. A constant, laminar flow velocity of the two-phase system can build up. The two-phase system can, for example, be formed in that separate educt streams are co-currently supplied into the bottom region of a tube reactor. In the bottom region, installations can be provided which ensure a drop-like distribution of the entering reactants. For example, nozzles, porous sinter plates or lances can be mounted as installations. The construction of a tube reactor is in principle known to a person skilled in the art.

The reaction is carried out within a tube reactor under laminar flow conditions with a Reynolds number of greater than or equal to 10 and less than or equal to 2320. The Reynolds number is a dimensionless coefficient and describes the characteristic of a flow. On the basis of the Reynolds number it can be seen whether a turbulent or a laminar flow (plug flow) is present. The critical Reynolds number characterizes the transition region from a laminar to a turbulent flow. In order to estimate the Reynolds number for the liquid/liquid two-phase system considered here, the mean flow velocity of all reactants on the flow cross-section (homogeneous model) is considered (Transportvorgange in der Verfahrenstechnik: Grundlagen und apparative Umsetzungen, Matthias Kraume, Springer Berlin, Heidelberg, 2nd edition, 2012, WO 2010/105892 A1).

In order to ensure the laminar flow condition within this Reynolds number range in the tube reactor, the mass flow of the reactants as well as the density and the dynamic viscosity of the reaction mixture are to be related with the hydraulic inner diameter of the tube reactor and to be controlled. This is implemented such that the required Reynolds number range, which indicates a laminar flow state, is not exceeded. The formula for the calculation of the Reynolds number is given by Equation (1)

$$Re = w\rho d/\eta \qquad (1)$$

wherein: w=mass flow [kg/h] of the reactants, ρ=density [kg/m³] of the reaction mixture, d=hydraulic inner diameter of the tube reactor [m] and η=dynamic viscosity [Pa·s] of the reaction mixture (VDI Wärmeatlas, 7th edition 1994, Lb1, Eq. (2); Grundlagen der Einphasen- und Mehrphasenströmungen, Heinz Bauer, Verlag Sauerländer, Aarau und Frankfurt am Main, 1971). The Reynolds number for a tubular flow at which a laminar flow transits into a turbulent flow is indicated by 2320. Assuming a homogeneous model, this classification also may apply here. Below this number a laminar flow state is present. According to the invention, a laminar flow is present in the tube reactor when a laminar flow profile prevails in at least 80%, preferably at least 90%, more preferably 100%, of the reactor volume. Surprisingly, it has been found that under these conditions excellent space-time yields are possible. For the case of a 100% laminar flow profile, the regions of supply of the educt and discharge of the product stream, which temporarily and spatially strongly restricted could exhibit a turbulent characteristic are not taken into consideration.

In a preferred embodiment of the method, the Reynolds number can be held constant within the tube reactor. It has proved to be particularly advantageous if the flow profile of the reaction mixture is purely laminar over wide ranges. Since reactor installations, such as static mixers or column packs, could increase the turbulence in the tube reactor, their use is less recommended. However, their use is not excluded according to the invention as long as the mass flow of the reactants flows through the tube reactor under laminar conditions. On the other hand, cooling coils or cooling fingers can be installed in the tube reactor, past which the mass flow of the reactants flows without disturbing the laminar state. Particularly advantageously, the tube reactor can be operated without installations. For this purpose, the aqueous formaldehyde solution, the alkanal and the organic solution of the catalyst can be mixed in a mixing element arranged upstream of the tubular reactor to give a total mass flow, which is then guided to the bottom of a tube reactor. For example, commercially available static mixing elements can be used for this purpose (for example, Sulzer or Kenicks mixers).

In a further embodiment of the method, the liquid/liquid two-phase system can be formed within the tube reactor by separate feeding at least one organic and at least one aqueous phase in a co-current flow. For a rapid and, where possible, defined formation of a laminar flow profile, the organic phase and the formaldehyde can be supplied into the reactor separated in an aqueous phase and in a co-current flow. In this way, a directed laminar flow can be formed, in which there is a sufficiently large phase boundary interface which allows a high space-time yield with simultaneously high selectivity.

According to a preferred embodiment of the method, the carboxylic acid can be fed into the reactor together dissolved in an organic solvent with the secondary amine. This embodiment with pre-dissolved catalyst consisting of carboxylic acid and amine can contribute to obtain higher space-time yields during the reaction in the tube reactor. Without being bound by theory, the pre-dissolution of the acid and the amine may lead to a more rapid equilibrium distribution of these components in the organic phase and also to a more rapid adjustment of the total phase equilibrium. The system is thereby stabilized and higher conversion rates are made available within a shorter reaction time. Suitable organic solvents are, for example, alcohols, esters or ethers, in particular with 6 to 12 carbon atoms. These solvents lead to a rapid distribution of the acid component and the amine in the alkanal, and this group of solvents can be separated again relatively easily from the main product stream after the reaction.

In a further embodiment, the solvent can be selected from the group consisting of monoalcohols with 6 to 12 carbon atoms or mixtures thereof. For the reaction, particularly of the short- to medium-chain aldehydes, this group of pre-solvents has proved particularly suitable. Particularly suitable are monoalcohols with 6 to 12 carbon atoms, such as heptanol, n-octanol, 2-ethylhexanol, n-nonanol or n-decanol. 2-Ethylhexanol has proven particularly suitable. The concentration of the secondary amine in the organic solvent may generally be from 30 to 50% by weight and the concentration of the carboxylic acid may be from 20 to 40% by weight. After the relatively concentrated solution has entered the tube reactor, the organic solution of the catalyst and the present alkanal combine into the organic phase and the desired molar ratios with respect to the alkanal of formula II are established.

According to an additional aspect of the method according to the invention, the reaction can be carried out at a temperature of greater than or equal to 70° C. and less than or equal to 150° C. Within this temperature range, high space-time yields can be obtained with good selectivities. Higher temperatures can be detrimental in terms of the operating costs and with respect to the formation of higher molecular by-products. Lower temperatures can result in unfavorable kinetics, which can have adverse effects on the volume of the tube reactor. Further preferably, the reaction can be carried out at a temperature of greater than or equal to 90° C. and less than or equal to 130° C. Possibly, a processing under pressure is advantageous in order to consider components with boiling points below the desired reaction temperature and to avoid boiling delays. Advantageously, the reaction can be carried out at an overpressure of 0.05, preferably 0.10, more preferably 0.15 and 0.20 MPa to less than 1 MPa, preferably less than 0.50 MPa. These pressure ranges can effectively avoid boiling delays, allow a uniform processing and can thereby contribute to a further increase in the yields.

A further embodiment of the method can be obtained in that no additional surface-active substances are present in the two-phase system. Without being bound by theory, in particular the acid-base catalysis according to the invention can contribute to a sufficient stabilization of the two-phase system, so that no further additives are necessary to form a sufficiently large phase boundary interface over the entire reactor volume even in a laminar flow regime. In this way, it is possible to dispense with the use of surface/boundary interface active substances such as surfactants, wetting agents or the like. This can facilitate the purification of the products and reduces the risk of accumulation of these substances in the system.

In a preferred embodiment, the tube reactor can be operated with a Reynolds number of greater than or equal to 50 and less than or equal to 500. As shown by the examples, very high space-time yields can be obtained particularly in the lower Reynolds number range with a laminar operation mode. This lower range, moreover, requires only a small amount of energy to be maintained and can thus contribute to lower plant investment costs and operating costs. Further preferably, the tube reactor can be operated with a Reynolds number of greater than or equal to 100 and less than or equal to 400.

According a further aspect of the method, the reactor load V/Vh (volume of the reaction mass per reactor volume and time) can be greater than or equal to $3.0\ h^{-1}$ and less than or equal to $42.0\ h^{-1}$. Surprisingly, a high conversion rate of alkanal of formula II with a consistently high selectivity can be achieved under the stated reaction conditions despite a comparatively high reactor load, corresponding to a shorter dwell time. The implementation according to the invention in a tube reactor under laminar conditions thus permits very high space-time yields of the desired 2-methylene alkanal. Outside the specified range possibly an insufficient conversion or an increased formation of high boiling solvents could occur. Further preferably, the ratio V/Vh may be greater than or equal to $5.0\ h^{-1}$ and less than or equal to $30.0\ h^{-1}$.

According to a further preferred embodiment of the method, the carboxylic acid can be selected from the group consisting of aliphatic or aromatic C2-C12 monocarboxylic acids. The group of short- to medium-chain monocarboxylic acids has proved to be particularly suitable for stabilizing the laminar system and for obtaining high space-time yields. Without being bound by theory, the carboxylic acids appear to integrate very well into the dispersed phase of short- to medium-chain alkanals and to diffuse therein. This can also contribute to higher product yields.

In a particularly preferred embodiment, the reaction of the alkanal with formaldehyde can be carried out in the presence of di-n-butylamine and butyric acid as catalyst.

According to a preferred embodiment of the method, the molar ratio of alkanal, formaldehyde in formalin and secondary amine can be in the range from 1:1:0.01 to 1:1.2: 0.07. This range of molar ratios between alkanal, formaldehyde in the aqueous formaldehyde solution and secondary amine show in particular a high selectivity and a good space-time yield in the tube reactor under laminar flow conditions, so that large quantities can be produced cost-effectively with low investment costs.

According to an additional aspect of the method, 0.01 to 0.07 equivalents of carboxylic acid can be reacted per mol of alkanal. This ratio of catalyst to alkanal has proved to be particularly suitable for achieving high conversion rates. Apparently, this amount is sufficient to provide high space-time yields in tube reactors. In particular, this ratio ensures both a sufficient stabilization of the laminar flow profile and a sufficient amount of catalyst (due to a sufficiently high mobility) within the aldehyde phase as a catalytic center for the aldehyde reaction. Furthermore, 0.025 to 0.05 equivalents of secondary amine and preferably also 0.025 to 0.05 equivalents of carboxylic acid can be used per mol of alkanal of the formula II in the feed product.

In a preferred embodiment of the method, the residue $R^1$ can be an aliphatic C5-C13 hydrocarbon residue. The present method can be particularly suitable for reacting these medium-chain aldehydes. Especially with the C5-C13 aldehydes, very high space-time yields can be achieved, wherein the proportion of non-utilizable higher-boiling by-products is extremely low. Without being bound by theory, the differences in the polarity of the aqueous formaldehyde phase and the aldehydes of this group appear to be such that the reaction takes place to a sufficient extent under laminar flow conditions along the liquid/liquid phase boundary. In particular, it may be advantageous to use only one or more aldehydes of the same C number in the reaction with formaldehyde. Despite the relatively large non-polar C-chains, adequate reaction speeds and a good space-time yield are obtained. Furthermore, it may be advantageous to have only one aldehyde with this residue definition in the reaction solution.

According to an additional aspect of the method, the molar ratio of carboxylic acid to secondary amine may be greater than or equal to 0.5 and less than or equal to 2. In order to obtain an overall fast reaction kinetics and consequently high space-time yields, the specified ratio between carboxylic acid and secondary amine has proven to be particularly suitable.

In a further preferred embodiment, one of the aldehydes used can be n-undecanal. The method according to the invention is particularly suitable for the reaction of mixtures containing 1-undecanal which are obtained in the hydroformylation of decene-1. Depending on the hydroformylation conditions, varying ratios of n-undecanal to 2-methyl decanal are obtained. In such mixtures, n-undecanal can be converted selectively and with a high space-time yield into the 2-methylene undecanal by the method according to the invention, wherein 2-methyl decanal remains unchanged because of the lower reactivity and can be separated by distillation. Likewise, initially n-undecanal can be separated from the hydroformylation mixture by distillation and then reacted with formaldehyde by the method according to the invention. 2-methylene undecanal can be derivatized by selective hydrogenation, for example, at the palladium or platinum contact into 2-methyl undecanal, which is an important raw material for the fragrance industry.

In a comparable manner, for example, methylene heptanal and subsequently 2-methyl heptanal can be derived from the hydroformylation product of hexene-1.

BRIEF DESCRIPTION OF THE DRAWINGS

Further details, features and advantages of the subject matter of the invention result from the dependent claims as well as from the following description of the figures and the associated examples. In the figures:

DETAILED DESCRIPTION OF THE INVENTION

Figure 1:
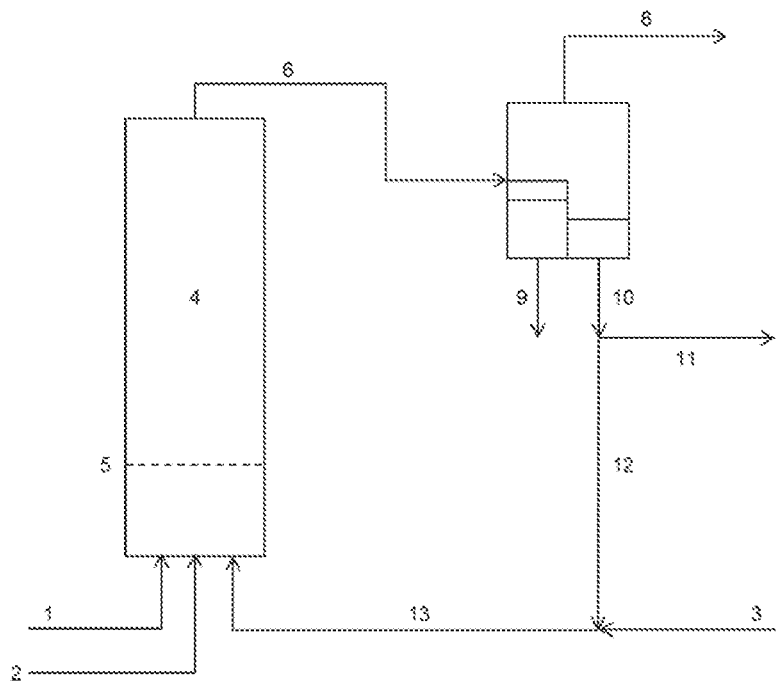
FIG. 1 schematically shows a possible embodiment of the method according to the invention with use of a tube reactor.

In FIG. 1 an aqueous formaldehyde solution is supplied via line 1, an organic solution containing a secondary amine and a carboxylic acid as catalyst for the Mannich condensation reaction is supplied via line 2 and fresh alkanal, mixed with the circulating flow, is supplied via line 3 at the bottom of a tube reactor 4. The water supplied with the aqueous formaldehyde solution forms the continuous phase within the tube reactor. The organic solution of the catalyst supplied via line 2 and the alkanal supplied via line 3 are separated into liquid drops by the devices 5 installed at the bottom of the tube reactor 4 and flow through the continuous aqueous phase as a dispersed organic phase due to the difference in density in the direction toward the reactor head. The sum of the mass flows supplied must be chosen such that a laminar flow state is formed within the tube reactor. Cooling coils or cooling fingers can be installed in the tube reactor for heat dissipation, but these do not interfere with the laminar flow behavior of the combined mass flows in the direction toward of the reactor head (not shown in FIG. 1). The liquid reactor effluent is passed at the reactor head via line 6 into a settling tank 7 in which the lighter organic phase separates from the heavier aqueous phase. Gaseous fractions are discharged via line 8. The settled aqueous phase, which still contains residual amounts of formaldehyde, is removed from the process via line 9. A further processing of the aqueous phase, for example by distillation, is optional.

The settled organic phase, which contains the desired 2-methylene alkanal, unreacted alkanal and likewise unreacted 2-methyl alkanal, are discharged via line 10 from the settling tank and a quantity is withdrawn therefrom as a partial stream via line 11. The raw product withdrawn can then be purified and used for further derivatization reactions, for example as a feed material for the selective hydrogenation. However, it is also possible to carry out a direct derivatization with subsequent purification.

The partial stream not withdrawn can be combined via line 12 in a closed loop with fresh alkanal supplied via line 3 and pumped via line 13 at the bottom of the reactor 4.

Figure 2:
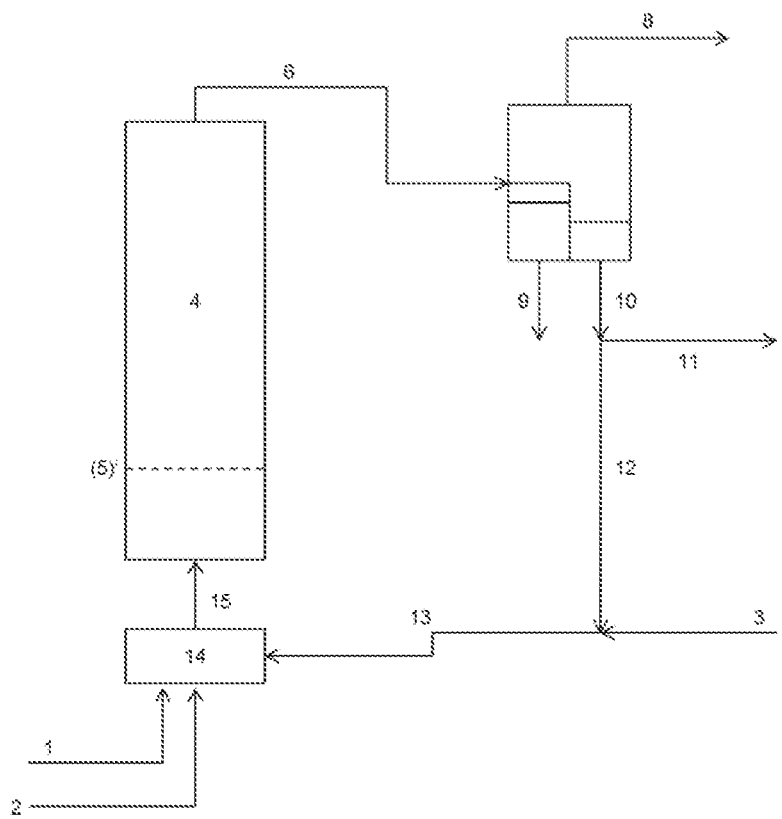
FIG. 2 schematically shows a further embodiment of the method according to the invention with use of a mixing element upstream of a tube reactor.

FIG. 2 shows a further embodiment of the method according to the invention with use of a mixing element upstream of the tube reactor. The aqueous formaldehyde solution supplied via line 1, the organic solution of the catalyst supplied via line 2 and the alkanal supplied via line 13 are dispersed in the static mixer 14. The multiphase mixture enters the bottom of the tube reactor 4 via line 15. The schematically indicated installations can be dispensed with in this embodiment, although devices in the bottom region of the tubular reactor are not excluded, as long as a laminar flow state of the tube reactor is ensured.

EXAMPLES

In a reactor having a volume of 0.191 l an aqueous formaldehyde solution (30% by weight), the catalyst mixture (consisting of 95.0 g of di-n-butylamine, 64.5 g of n-butyric acid, 50.1 g 2-ethylhexanol) and the aldehyde (undecanal with 67% or 91% n-undecanal content) are each supplied continuously separately but co-currently via the reactor bottom. If no static mixer is used, the material streams can be separately but co-currently guided to the bottom of the tube reactor. If a static mixer is used (for example Sulzer mixer of type SMX DN4), the mixing element can be installed outside the reactor upstream of the reactor bottom. Therein the aqueous solution and the organic solutions can be mixed with one another, and subsequently the liquid multi-phase system with the dispersed organic phase can be added to the tube reactor. In both embodiments, the dispersed organic phase flows through the continuous aqueous phase in the form of droplets.

The multiphase reaction mixture can be removed at the reactor head and introduced into a settling tank. From the separated liquid phases an organic circuit stream is returned to the tube reactor. The non-recycled aqueous phase is discharged while the non-recycled organic phase was analyzed by gas chromatography for its valuable product content.

The reaction conditions, the continuous supply of the feed materials and the circulation flows were adjusted according to the conditions specified in table 1 below. Table 1 also shows the composition determined by gas chromatography of the organic product, anhydrous, specified in %. The tests were carried out at an overpressure of 0.2 MPa.

TABLE 1 results of the reaction of undecanal with formalin according to the invention

| | Experiment | | | | | | | | |
|---|---|---|---|---|---|---|---|---|---|
| | 1 | 2 | 3 | 4 | 5 | 6 | 7 | 8 | 9 |
| Temperature [° C.] | 125 | 125 | 125 | 100 | 125 | 125 | 115 | 115 | 125 |
| Pressure [bar] | 2.0 | 2.0 | 2.0 | 2.0 | 2.0 | 2.0 | 2.0 | 2.0 | 2.0 |
| V/Vh (undecanal + circuit) [1/h] | 14.2 | 14.3 | 14.3 | 14.3 | 13.8 | 13.3 | 13.8 | 13.7 | 13.7 |
| Formalin [g/h] | 47.0 | 47.0 | 47.0 | 46.7 | 58.0 | 28.0 | 58.0 | 84.0 | 84.0 |
| Undecanal [g/h] | 109.0 | 108.9 | 109.0 | 109.2 | 98.1 | 48.0 | 98.0 | 142.4 | 142.8 |
| Catalysator solution [g/h] | 2.9 | 4.5 | 5.9 | 5.8 | 7.0 | 4.5 | 7.9 | 10.1 | 10.4 |
| Circuit [g/h] | 2000 | 2000 | 2000 | 2000 | 2000 | 2000 | 2000 | 2000 | 2000 |
| Ratio n-C11-al to formalin | 1-1.09 | 1-1.09 | 1-1.09 | 1-1.09 | 1-1.09 | 1-1.09 | 1-1.09 | 1-1.09 | 1-1.09 |
| Ratio n-C11-al to Bu2NH | 1-0.025 | 1-0.04 | 1-0.05 | 1-0.05 | 1-0.05 | 1-0.05 | 1-0.05 | 1-0.05 | 1-0.05 |
| ratio Bu2NH to n-C4 acid | 1-1 | 1-1 | 1-1 | 1-1 | 1-1 | 1-1 | 1-1 | 1-1 | 1-1 |
| Percentage n-undecanal in undecanal | 67 | 67 | 67 | 67 | 91 | 91 | 91 | 91 | 91 |
| Analysis of the product stream [%] | | | | | | | | | |
| Forerun | 0.36 | 0.05 | 0.04 | 0.05 | 0.05 | 0.05 | 0.03 | 0.06 | 0.11 |
| n-butyric acid | 0.40 | 0.60 | 0.81 | 0.87 | 0.81 | 0.84 | 0.83 | 0.94 | 0.91 |
| Intermediate run 1 | 0.17 | 0.16 | 0.16 | | | | | | |
| n-decane max. | 0.08 | 0.08 | 0.07 | 0.05 | | <0.01 | 0.02 | | |
| Decene range | 0.29 | 0.32 | 0.27 | 0.43 | 0.26 | 0.22 | 0.32 | 0.22 | 0.37 |
| 2-EH-ol | 0.77 | 1.08 | 1.40 | 1.40 | 1.86 | 1.77 | 1.66 | 1.70 | 1.60 |
| Intermediate run 2 | 0.24 | 0.24 | 0.23 | 0.19 | 0.45 | 0.16 | 0.39 | 0.27 | 0.30 |
| 2-EH acid | 0.03 | 0.03 | 0.03 | 0.02 | | | | | |
| 2-butylheptanal | 0.05 | 0.05 | 0.04 | 0.04 | 0.01 | <0.01 | 0.01 | | 0.01 |
| 2-propyloctanal | 0.08 | 0.07 | 0.07 | 0.07 | 0.01 | 0.01 | 0.01 | 0.01 | 0.01 |
| 2-ethylnonanal | 0.82 | 0.78 | 0.72 | 0.83 | 0.21 | 0.20 | 0.19 | 0.21 | 0.19 |
| 2-methyldecanal | 26.48 | 26.10 | 25.11 | 26.93 | 4.34 | 4.87 | 4.35 | 4.55 | 4.14 |
| Intermediate run 3 | 0.26 | 0.25 | 0.33 | 0.37 | 0.15 | 0.18 | 0.20 | 0.16 | 0.16 |
| n-undecanal | 10.72 | 8.98 | 6.10 | 10.60 | 1.53 | 2.73 | 0.82 | 2.49 | 1.36 |
| Intermediate run 4 | 3.82 | 3.72 | 4.67 | 0.05 | 0.07 | 0.07 | 0.06 | 0.11 | 0.10 |
| 2-methyldecanol | 0.12 | 0.11 | 0.11 | 0.12 | 0.04 | 0.04 | 0.05 | 0.02 | 0.03 |
| 2-methylen undecanal | 25.06 | 28.28 | 36.96 | 27.54 | 68.20 | 66.05 | 71.22 | 64.45 | 69.31 |
| 2-hydroxymethyl undecanal | 25.45 | 24.70 | 18.44 | 24.36 | 5.43 | 2.59 | 5.14 | 12.39 | 10.73 |
| Final run | 4.80 | 4.40 | 4.44 | 6.08 | 16.58 | 20.22 | 14.70 | 12.42 | 10.67 |
| Sum | 100 | 100 | 100 | 100 | 100 | 100 | 100 | 100 | 100 |
| Conversion rate of n-undecanal | 84% | 87% | 91% | 84% | 98% | 97% | 99% | 97% | 99% |
| Selectivity* | 90% | 91% | 91% | 92% | 82% | 77% | 84% | 86% | 89% |
| Yield* | 75% | 79% | 83% | 77% | 81% | 75% | 84% | 84% | 88% |

*= Formed amount of 2-methylene undecanal + 2-hydroxymethyl undecanal in % with respect to the amount of n-undecanal used It is clear from Table 1 that high yields can be obtained in the course of a continuous production process within a tube reactor in a laminar operation mode by acid-base catalysis. The yields are all above 75%, wherein generally high conversion rates of more than 84% are realized. In sum, these give high space-time yields, which are not available in this scale either by batch or continuous operation modes in agitated vessels/cascades.

By varying the total mass flow of the reactants, the Reynolds number can be specifically adjusted in such a way that a laminar flow state is established in the tube reactor. For the experiments with the highest reactor loading (experiments 8 and 9 in table 1), the Reynolds number is 176 (see table 2) and thus in the laminar flow range (less than 2320). In the examples 1-7, a lower feed mass flow was used. As a result, a smaller Reynolds number is obtained from equation (1). Thus, stable laminar flow conditions are present in the listed examples.

TABLE 2

| Hydraulic parameters, exemplary for example experiment 8: | | |
| --- | --- | --- |
| Density ρ | [kg/m³] | 990 |
| Dynamic viscosity η | [Pa s] | 0.0005 |
| Hydraulic inner diameter d | [m] | 0.009 |
| Mass flow of the reactants | [kg/h] | 2.24 |
| Reynolds number | | 176 |

The reaction product obtained from the experiments can be separated in subsequent purification steps and then partially hydrogenated at the palladium or platinum catalyst. 2-methyldecanal is present unchanged in the hydrogenated reaction mixture and the desired 2-methylundecanal can be distilled off fractionally. 2-Methylundecanal is a valuable product for the fragrance industry.

The invention claimed is:

1. A method for producing 2-methylene alkanals of the general formula I

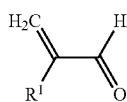

Formula I wherein $R^1$ is an aliphatic residue, by reacting alkanals of the general formula II

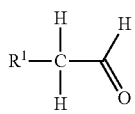

Formula II with an aqueous formaldehyde solution in the presence of at least one secondary amine and at least one carboxylic acid, characterized in that the educts are reacted in a liquid/liquid two-phase system, wherein the reaction is carried out continuously within a tube reactor under laminar flow conditions with a Reynolds number of greater than or equal to 10 and less than or equal to 2320.

2. The method according to claim 1, wherein the Reynolds number is kept constant within the tube reactor.

3. The method according to claim 1, wherein the liquid/liquid two-phase system is formed by separately introducing at least one organic and at least one aqueous phase in a co-current flow into the tube reactor.

4. The method according to claim 1, wherein the carboxylic acid is introduced into the reactor together with the secondary amine dissolved in an organic solvent.

5. The method according claim 4, wherein the solvent is selected from the group consisting of mono-alcohols with 6 to 12 carbon atoms or mixtures thereof.

6. The method according to claim 1, wherein the reaction is carried out at a temperature of greater than or equal to 70° C. and less than or equal to 150° C.

7. The method according to claim 1, wherein no additional surface-active substances are present in the two-phase system.

8. The method according to claim 1, wherein the tube reactor is operated with a Reynolds number of greater than or equal to 50 and less than or equal to 500.

9. The method according to claim 1, wherein the reactor load V/Vh with respect to the total mass flow of reactants is greater than or equal to $3.0\ h^{-1}$ and less than or equal to $42.0\ h^{-1}$.

10. The method according to claim 1, wherein the carboxylic acid is selected from the group consisting of aliphatic or aromatic C2-C12 monocarboxylic acids.

11. The method according to claim 1, wherein the molar ratio of alkanal, formaldehyde in the formalin and secondary amine is in the range from 1:1:0.01 to 1:1.2:0.07.

12. The method according to claim 1, wherein the residue $R^1$ is an aliphatic C5-C13 hydrocarbon residue.

13. The method according to claim 1, wherein at least two different alkanals with the same C number and C greater than or equal to 2, are reacted, wherein at least one of the alkanals has a structure according to formula II.

14. The method according to claim 1, wherein the molar ratio of carboxylic acid to secondary amine is greater than or equal to 0.5 and less than or equal to 2.

15. The method according to claim 13, wherein one of the alkanals used is n-undecanal.

16. The method according to claim 2, wherein the reaction is carried out at a temperature of greater than or equal to 70° C. and less than or equal to 150° C.

17. The method according to claim 2, wherein the tube reactor is operated with a Reynolds number of greater than or equal to 50 and less than or equal to 500.

18. The method according to claim 2, wherein the reactor load V/Vh with respect to the total mass flow of reactants is greater than or equal to $3.0\ h^{-1}$ and less than or equal to $42.0\ h^{-1}$.

19. The method according to claim 2, wherein the molar ratio of alkanal, formaldehyde in the formalin and secondary amine is in the range from 1:1:0.01 to 1:1.2:0.07.

20. The method according to claim 1, wherein no surface active substances are added;
the tube reactor is operated with a Reynolds number of greater than or equal to 50 and less than or equal to 500 at a temperature of greater than or equal to 70° C. and less than or equal to 150° C.; the reactor load V/Vh with respect to the total mass flow of reactants is greater than or equal to $3.0\ h^{-1}$ and less than or equal to $42.0\ h^{-1}$ and the molar ratio of alkanal, formaldehyde in the formalin and secondary amine is in the range from 1:1:0.01 to 1:1.2:0.07.

* * * * *